United States Patent [19]

Konomura

[11] Patent Number: 4,475,539
[45] Date of Patent: Oct. 9, 1984

[54] ENDOSCOPIC TELEVISION APPARATUS

[75] Inventor: Yutaka Konomura, Tokyo, Japan

[73] Assignee: Olympus Optical Co., Ltd., Tokyo, Japan

[21] Appl. No.: 312,791

[22] Filed: Oct. 19, 1981

[30] Foreign Application Priority Data

Oct. 28, 1980 [JP] Japan .................................. 55-150975
Oct. 28, 1980 [JP] Japan .................................. 55-150976

[51] Int. Cl.³ .................................................. A61B 1/06
[52] U.S. Cl. ........................................... 128/6; 358/98
[58] Field of Search .............................. 128/4, 5, 6-8; 354/62; 358/98, 22

[56] References Cited

U.S. PATENT DOCUMENTS

| 2,593,925 | 4/1952 | Sheldon | 128/4 |
| 3,136,310 | 6/1964 | Meltzer | 128/6 |
| 4,185,295 | 1/1980 | Hess et al. | 358/22 |
| 4,261,344 | 4/1981 | Moore et al. | 128/6 |
| 4,277,168 | 7/1981 | Oku | 128/4 |
| 4,331,132 | 5/1982 | Mukasa | 128/6 |

FOREIGN PATENT DOCUMENTS

| 885770 | 1/1954 | Fed. Rep. of Germany | 128/6 |
| 2741714 | 3/1978 | Fed. Rep. of Germany | 128/6 |
| 2633742 | 7/1979 | Fed. Rep. of Germany | 128/6 |

OTHER PUBLICATIONS

Patent Associated Literature, "Hardy Endoscope Color TV System Using New Chalnicon Pickup Tube", Fukui and Hosoi, May/Jun. 1975.

Primary Examiner—Edward M. Coven
Assistant Examiner—Max F. Hindenburg

[57] ABSTRACT

An optical filter member composed of a plurality of ND filters having different transmission factors and arranged circumferentially at regular intervals is disposed between a light source and a light guide of an endoscope. When the optical filter member is rotated, a light beam with periodically varying luminance is transmitted through the light guide to illuminate an object inside a body cavity. Images of the object corresponding to different luminances are converted severally into video signals by a television camera. A signal component within a given level range is extracted from each of these video signals by a limiter. The signal components of the video signals are composed into video data to be supplied to a display. The display indicates the video data as an image with proper contrast.

6 Claims, 5 Drawing Figures

ENDOSCOPIC TELEVISION APPARATUS

BACKGROUND OF THE INVENTION

This invention relates to an endoscopic television apparatus capable of television-photographing inside a patient's body by using an endoscope.

In endoscopic television-observation of inside a patient's body by means of an endoscope, the output of a light supply unit for supplying illumination light to the endoscope is generally controlled according to the brightness of the region of interest, since th optical density of an image formed on a monitor television may change according to the brightness of the region of interest. In a prior art apparatus, the quantity of light transmitted by the whole or part of an image guide as an image transmitting optical system of the endoscope is measured, and the output of the light supply unit is controlled so as to keep such quantity constant.

In endoscopic television-photographing, however, the quantity of light will greatly change according to the distance between the endoscope and the region of interest so that the television apparatus cannot exercise its faculties despite the aforesaid control of the output of the light supply unit, since the range of photographing distance is wide although the space inside the patient's body is narrow. As a result, an image of a region of the body near the endoscope may become pure white, whereas an image of a region distant from the endoscope may turn out deep-black. Thus, despite the control of the output of the light supply unit, the range to allow satisfactory observation cannot help being quite narrow.

SUMMARY OF THE INVENTION

The object of this invention is to provide an endoscopic television apparatus capable of producing and endoscopic television image with proper general contrast.

According to this invention, there is provided an endoscopic television apparatus which comprises a light supply unit for illuminating an object with an illumination light with periodically varying luminance through an endoscope, a video camera unit for producing video signals corresponding to images of the object illuminated with different luminances in synchronism with different luminance periods, a limiter for allowing the signal components in a predetermined range of levels, of the video signals from the camera unit, to pass therethrough, memory means for storing the video signal components passed through the limiter to form a video signal, and a display unit for displaying the video signal read out from the memory means.

DETAILED DESCRIPTION OF THE PREFERRED EMBODIMENTS

Figure 1:
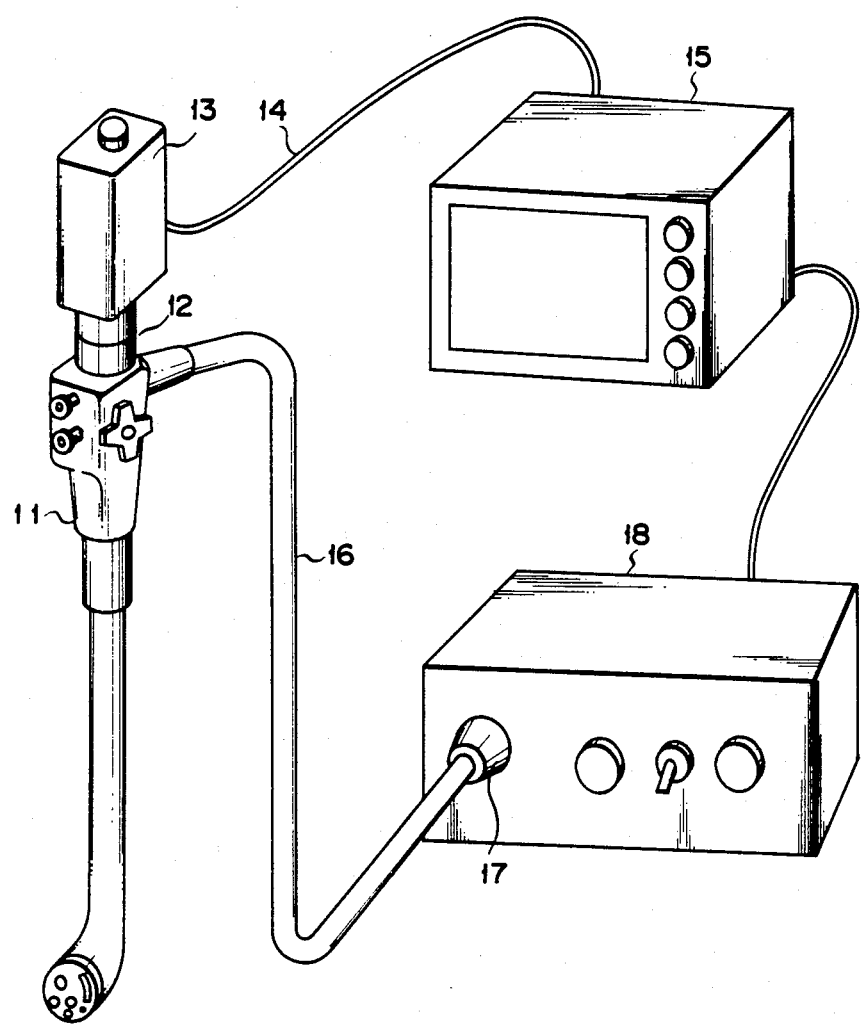
FIG. 1 is a perspective view of an endoscopic television apparatus according to an embodiment of this invention.

Referring now to the drawing of FIG. 1, a television camera 13 is removably attached to an eyepiece section 12 of an endoscope 11. A cord 14 of the television camera 13 is connected with a television monitor 15. A connector 17 of a universal cord 16 of the endoscope 11 is removably connected with a light supply unit 18.

Figure 2:
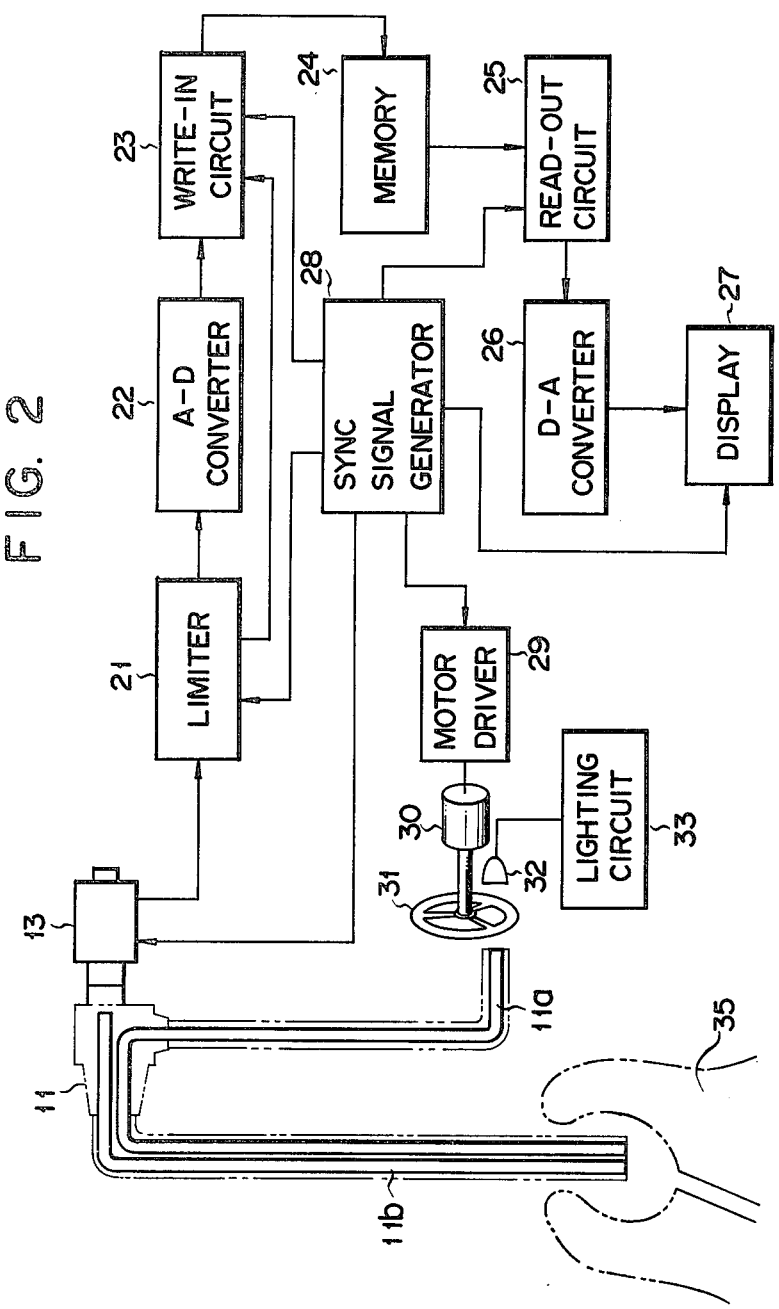
FIG. 2 is a block circuit diagram of the endoscopic television apparatus of FIG. 1.
Figure 3:
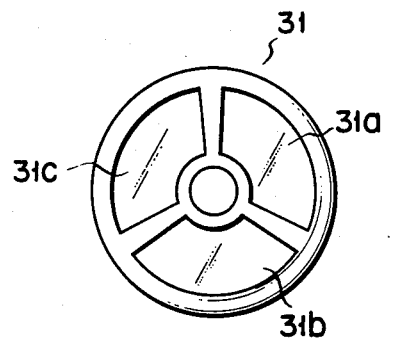
FIG. 3 is a plan view of an optical fiber shown in FIG. 2.

As shown in FIG. 2, the output end of the television camera 13 is connected to the input terminal of a limiter 21 of the television monitor 15. The output terminal of the limiter 21 is connected to the input terminal of a write-in circuit 23 through an A-D converter 22, and connected directly to the write-in control input terminal of the write-in circuit 23. The write-in circuit 23 is connected to the write-in terminal of a memory 24. The read-out terminal of the memory 24 is connected to the input terminal of a read-out circuit 25. The output terminal of the read-out circuit 25 is connected to the input terminal of a cathode-ray-tube (CRT) display 27 through a D-A converter 26. Sync signal output terminals of a sync signal generator 28 are connected to the respective sync signal input terminals of the television camera 13, the limiter 21, the write-in circuit 23, the read-out circuit 25, the display 27, and a motor driver 29. The output terminal of the motor driver 29 is connected to a motor 30 whose shaft is coupled to a rotatable optical filter member 31. The rotatable optical filter member 31 is disposed between a light guide 11a of the endoscope 11 and a light source 32, and has three ND filters 31a, 31b and 31c having different transmission factors and arranged at regular intervals, as shown in FIG. 3.

Figure 4:
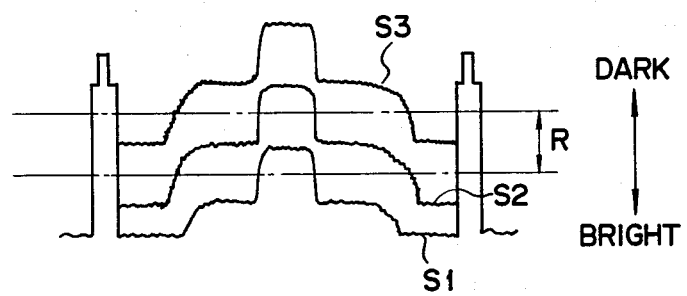
FIG. 4 shows video signals.

In the endoscopic television apparatus of the above-mentioned construction, when the light source 32 is turned on by a lighting circuit 33, light from the light source 32 is projected on light guide 11a through the optical filter member 31. This light is transmitted through the light guide 11a to illuminate a body 35. An image of the body 35 is transmitted through an image guide 11b to be formed on the television camera 13. At this time, the motor driver 29 rotates the motor 30 in synchronism with sync signals from the sync signal generator 28. When the optical filter member 31 is rotated at 10 rps, the density of the light from the light source 32 projected on the light guide 11a through the optical filter member 31 is changed periodically, that is, with a period of 1/30 second by the ND filters 31a, 31b and 31c of the optical filter member 31. In other words, body images with different luminances are formed on the television camera 13 at intervals of 1/30 second. The television camera 13 converts the body images corresponding to source light beams transmitted through the ND filters 31a, 31b and 31c into video signals in synchronism with the sync signal. The television camera 13 delivers a video signal for one frame with every 1/30 second, and produces video signals for three frames while the optical filter member 31 makes one revolution. FIG. 4 shows superposed video signals S1, S2 and S3 for three frames. The video signals S1, S2 and S3 correspond to body images illuminated with light beams transmitted through the ND filters 31a, 31b and 31c, respectively. The images corresponding to the signals S1, S2 and S3 are given according to brightness. In other words, the ND filters 31a, 31b and 31c are named in order of transmission factor.

When applied successively to the limiter 21, the signal components of the video signals S1, S2 and S3 from the television camera 13 in a predetermined range R of levels pass through the limiter 21 as shown in FIG. 4. Namely, dark, medium and bright signal components are extracted from the signals S1, S2 and S3, respectively. The signal components extracted by the limiter 21 are converted into digital signal components by the A-D converter, and written as video data in the memory 24 by the write-in circuit 23. When all the signal components of the video signals S1, S2 and S3 are written in the memory 24, the memory 24 is concluded to have stored the signal components of the video signals S1, S2 and S3 in a composite form and with reasonable contrast property. Accordingly, video data read out from the memory 24 by the read-out circuit 25 corresponds to a body image with proper general contrast. Thus, when the video data is converted into an analog video signal by the D-A converter 26 to be displayed on the display 27, the display 27 exhibits the body image with proper general contrast irrespective of the distance from the region of interest.

Figure 5:
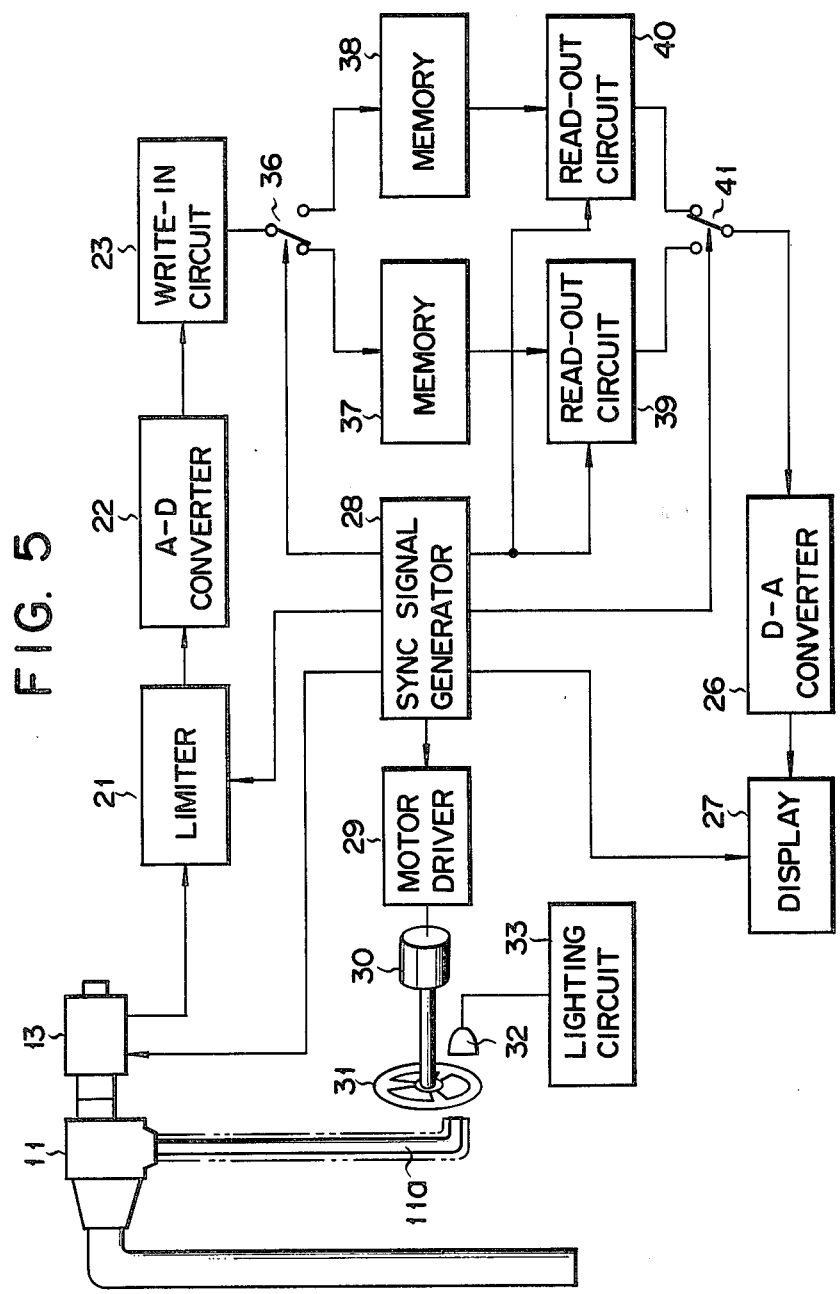
FIG. 5 is a circuit diagram of an endoscopic television apparatus according to another embodiment of the invention.

Referring now to FIG. 5, there will be described another embodiment of the invention. In FIGS. 2 and 5, like reference numerals are used to designate like portions. The output terminal of the write-in circuit 23 is connected to the common terminal of a changeover switch 36 whose changeover terminals are connected severally to memories 37 and 38. The read-out terminals of the memories 37 and 38 are connected to the changeover terminals of a changeover switch 41 through read-out circuits 39 and 40, respectively. The common terminal of the changeover switch 41 is connected to the input terminal of the D-A converter 26.

In the embodiment of FIG. 5, video data stored in the memory 38 is read out by the read-out circuit 40, and applied to the D-A converter 26 via the changeover switch 41 while video signals for three frames produced correspondingly to one revolution of the optical filter member 31, that is, video signals for three frames corresponding to the three ND filters 31a, 31b and 31c are being written in, for example, the memory 37 via the changeover switch 36. Analog video signals from the D-A converter 26 are displayed in the display 27. When the changeover switches 36 and 41 are then shifted in synchronism with a sync signal, newly produced video signals are stored in the memory 38. In the meantime, the previously stored video data is read out from the memory 37 by the read-out circuit 39, and transferred to the display 27 through the changeover switch 41 and the D-A converter 26. Thus, in this embodiment, the memories 37 and 38 are shifted in synchronism with the sync signal so that storage of a new video signal and read-out of a preceding video signal are executed simultaneously. Also in this embodiment, the signal components of video signals for three frames obtained with the use of the three ND filters 31a, 31b and 31c are synthesized with satisfactory contrast to provide a body image of good quality on the whole.

According to this invention, as described above, an object is illuminated with light with a density varying periodically, and signal components within a given level range are extracted from video signals each corresponding to each light density, and are composed to reproduce an image. Accordingly, it is possible to obtain an image with proper general contrast irrespective of the distance from the region of the object being viewed.

Although the optical filter member is composed of three ND filters in the above-mentioned embodiment, it may be composed of any number of filters but one. Further, it is not essential to use the aforementioned optical filter member for changing the light density, and the luminance of the light source may be changed periodically, for example.

What is claimed is:

1. An endoscopic television apparatus comprising:
   a light supply unit for periodically emitting light beams of different luminances;
   an endoscope including a light guide for leading the light beams from said light supply unit to an object and an image guide for transmitting images of the object subjected to the light beams of different luminances;
   a camera unit for converting the images transmitted by the image guide of said endoscope into video signals of different brightnesses corresponding to the different luminances;
   means for extracting signal components within a given level range from each of the video signals from said camera unit;
   synthesizing means for synthesizing the signal components extracted by said signal component extracting means to form video data; and
   means for displaying the composite video signal from said synthesizing means as an image of said object.

2. An endoscopic television apparatus according to claim 1, wherein said light supply unit is composed of a light source emitting a light beam with a fixed luminance, and a plurality of ND filters with different transmission factors through which the light beam from said light source is transmitted with a fixed period.

3. An endoscopic television apparatus according to claim 1, wherein said light supply unit is composed of a light source emitting a light beam with a fixed luminance, an optical filter member formed of a plurality of ND filters having different transmission factors and arranged circumferentially at regular intervals and rotatably disposed between said light source and said light guide, and driving means for rotating said optical filter member at fixed a speed.

4. An endoscopic television apparatus according to claim 1, wherein said signal component extracting means is composed of a limiter to pass the signal components of the video signals from said camera unit within the given level range.

5. An endoscopic television apparatus according to claim 1, wherein said synthesizing means is composed of at least one memory for successively storing the signal components from said signal component extracting means, and means for reading out the signal components from said memory as video data.

6. An endoscopic television apparatus according to claim 1, wherein said synthesizing means is composed of first and second memories and switch means periodically switching between said first and second memories, so that a signal component is read out from one of said first and second memories while another signal component is being written in the other memory.

* * * * *